(12) United States Patent
Mehnert et al.

(10) Patent No.: US 6,852,229 B2
(45) Date of Patent: Feb. 8, 2005

(54) METHOD FOR PREPARING HIGH-PURITY IONIC LIQUIDS

(75) Inventors: Christian P. Mehnert, Clinton, NJ (US); Nicholas C. Dispenziere, Wall, NJ (US); Raymond A. Cook, Bethlehem, PA (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 86 days.

(21) Appl. No.: 10/277,420

(22) Filed: Oct. 22, 2002

(65) Prior Publication Data

US 2004/0074842 A1 Apr. 22, 2004

(51) Int. Cl.[7] .............................................. B01D 11/04
(52) U.S. Cl. ..................... 210/634; 210/767; 210/774; 210/777; 210/804; 210/806; 429/199; 502/224
(58) Field of Search ................................ 210/634, 639, 210/644, 767, 774, 777, 804, 806, 778; 252/62.2; 429/198, 199; 502/224

(56) References Cited

U.S. PATENT DOCUMENTS

| | | | |
|---|---|---|---|
| 3,338,903 A | 8/1967 | Harrison ..................... 260/271 |
| 4,623,479 A | 11/1986 | Kucharska et al. ......... 252/350 |
| 5,053,537 A | 10/1991 | Gitzel et al. ................ 564/8 |
| 5,273,840 A | 12/1993 | Dominey .................... 429/192 |
| 5,349,067 A | 9/1994 | Nakano et al. ............. 546/347 |
| 5,378,445 A | 1/1995 | Salmon et al. ............. 423/301 |
| 5,399,624 A | * | 3/1995 | Glaser et al. ............... 525/289 |
| 5,705,696 A | 1/1998 | King, Jr. ..................... 564/296 |
| 5,731,101 A | * | 3/1998 | Sherif et al. ................ 429/102 |
| 5,827,602 A | * | 10/1998 | Koch et al. ................. 429/328 |
| 5,856,513 A | 1/1999 | Ue et al. ..................... 548/347.1 |
| 5,874,638 A | 2/1999 | Chauvin et al. ............ 568/454 |
| 5,892,124 A | 4/1999 | Olivier et al. .............. 568/374 |
| 5,965,054 A | 10/1999 | McEwen et al. ........... 252/62.2 |
| 5,993,767 A | 11/1999 | Willmann et al. .......... 423/301 |
| 6,103,908 A | 8/2000 | Bahrmann et al. ......... 546/347 |
| 6,169,209 B1 | 1/2001 | Harada et al. ................ 568/9 |
| 6,245,918 B1 | 6/2001 | Olivier et al. ........... 548/335.1 |
| 6,379,634 B1 | * | 4/2002 | Fields et al. .................... 423/4 |
| 6,552,232 B2 | * | 4/2003 | Mehnert et al. ............ 568/463 |
| 6,637,737 B1 | * | 10/2003 | Beecherl et al. ............... 269/71 |
| 6,774,240 B2 | * | 8/2004 | Seddon et al. ........... 548/347.1 |

FOREIGN PATENT DOCUMENTS

| | | |
|---|---|---|
| EP | 0882698 | 12/1998 |
| EP | 0924182 | 6/1999 |
| EP | 0748653 | 1/2000 |
| EP | 0776880 | 1/2000 |
| EP | 1074308 | 2/2001 |
| EP | 1106575 | 6/2001 |
| WO | WO 9916776 | 4/1999 |

\* cited by examiner

Primary Examiner—Joseph Drodge
(74) Attorney, Agent, or Firm—Paul E. Purwin

(57) ABSTRACT

A method for preparing a high-purity ionic liquid having a pH value of 7 and an elemental analysis deviation of less than 0.5 wt % between a calculated elemental analysis and a found elemental analysis for each of carbon, hydrogen and nitrogen, wherein the method comprises forming a monophasic or biphasic mixture of an ionic liquid and an inert liquid. When the monophasic mixture is formed, it is filtered to yield a filtrate from which the high-purity ionic liquid is recovered. When the biphasic mixtures is formed, it is separated into an aqueous phase and ionic liquid phase, whereby the ionic liquid phase is filtered to yield a filtrate from which the high-purity ionic liquid is recovered. Furthermore, the present purification procedure can be used for the clean-up of a contaminated ionic liquid by extracting it into a polar extractant to form an extract containing the ionic liquid. Water traces are removed from the extract. Then, the extract is filtered and the high-purity ionic liquid is recovered from the filtered extract.

42 Claims, 2 Drawing Sheets

Figure 1
(a) 
(b) 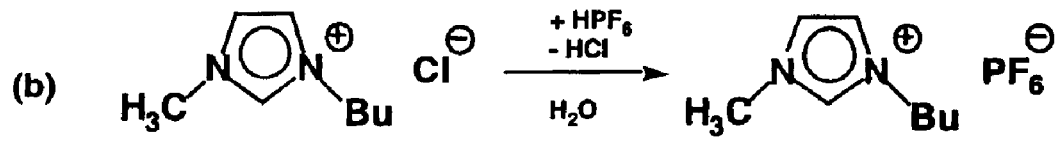
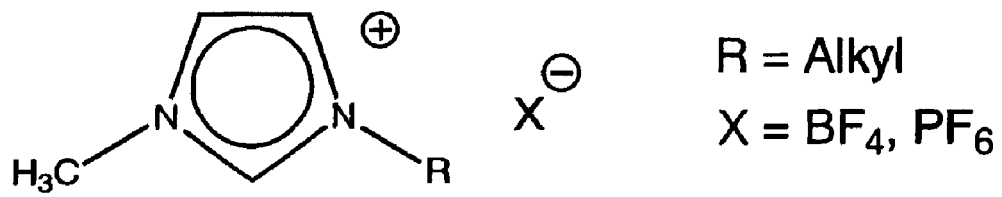
R = Alkyl
X = BF$_4$, PF$_6$
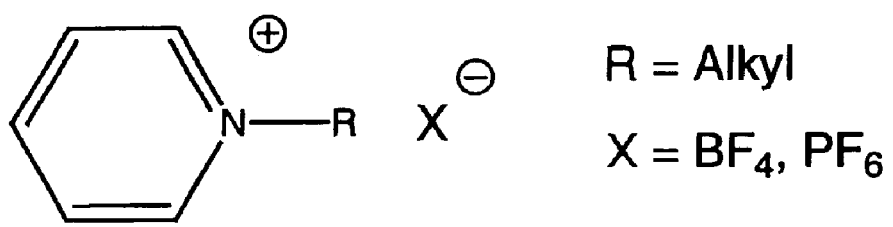
R = Alkyl
X = BF$_4$, PF$_6$
Figure 2

METHOD FOR PREPARING HIGH-PURITY IONIC LIQUIDS

BACKGROUND OF THE INVENTION

1. Field of the Invention

The present invention relates to a method for the production of high-purity ionic liquids. In particular, the instant invention is directed to making high-purity ionic liquids to prevent the destruction of the catalyst and the ionic liquid during catalytic reactions. The present invention also relates to a method for the purification of recycled or contaminated ionic liquid media.

2. Description of the Related Art

Ionic liquids are currently investigated for a variety of different applications, e.g., solvent media for homogeneous and heterogeneous catalysis, extraction/separation processes, membrane technology, polymerization media, lubricants, etc. Many of these applications require high-purity ionic liquids. Although the preparation of ionic liquids has been established, certain methods have led to the production of contaminated products. The use of "impure" ionic liquids results in the destruction of the catalyst and leads to the formation of undesired products.

Most of the known ionic liquid preparations utilize acids to introduce the corresponding anions. Although most of the ionic liquids are produced by this procedure, they are often contaminated with trace amounts of acid/base and/or halides. An investigation of commercially available materials showed such contamination. Furthermore, the olefinic starting material can be oligomerized into undesired side-products due to the acid contamination. Other studies have shown that the presence of residual chlorine traces in ionic liquids act as a very potent catalyst poison. Therefore it is highly desirable to have a synthesis method that enables the preparation of high-purity ionic liquids.

In most of the known ionic liquid preparations, an alkylimidazolium or pyridinium halide is treated with an acid to introduce the corresponding anion. In other words, in conventional preparations FIG. 1, equation (a) the imidazolium or pyridinium halide ($M^+X^-$) is converted via acid treatment ($H^+A^-$) to form the corresponding ionic liquid ($M^+A^-$) and an acid ($H^+X^-$). FIG. 1, equation (b) shows a typical preparation of the ionic liquid 1-butyl-3-methyl-imidazolium hexafluorophosphate. The imidazolium chloride is dissolved in an aqueous solution and then treated with an equivalent of $HPF_6$ in water. After several hours of stirring, the ionic liquid separates out as a second liquid phase. The resulting phases are separated and the ionic liquid isolated. Further purification of the ionic liquid involved additional washings with water or basic solutions. It is known to be very difficult to remove all the acid traces by either water washings or by neutralization. In both cases, one obtains an ionic liquid that has either acid or base contaminants. In the different methods of using acids for the preparation of ionic liquids, all led to the decomposition of both the catalyst and ionic liquid when applied in catalysis.

With respect to further purification sequences, most of the published methods do not incorporate any further steps. This common practice is also reflected in the low purity of the commercially available materials. Analysis of such samples showed the presence of acid and halide contaminants. Therefore, there is a need in the art for a method for preparing high-purity ionic liquids.

For example, most of the ionic liquids used in hydroformylation catalysis contain anions like tetrafluoroborate or hexafluorophosphate. The usage of slightly acidic ionic liquids—i.e., those containing trace amounts of unreacted starting material, like the acid $HPF_6$—in hydroformylation catalysis initiates the decomposition of the ionic liquid anions and results in the formation of hydrofluoric acid (HF). This very aggressive acid destroys both the catalyst and the ionic liquid. Moreover, the olefinic substrate is oligomerized to undesired side-products.

Hence there is a need in the art for a method to make a high-purity ionic liquid that will not decompose or adversely affect the performance of a reaction catalyst. There is also a need in the art for a method to purify contaminated ionic liquids.

BRIEF SUMMARY OF THE INVENTION

The present invention is for a method for preparing a high-purity ionic liquid having a pH value of 7 and an elemental analysis deviation of less than 0.5 wt % between a calculated elemental analysis and a found elemental analysis for each of carbon, hydrogen and nitrogen. The ionic liquids formed by the novel process have been used in catalysis (hydroformylation and hydrogenation reactions) without any sign of decomposition. This novel preparation method and purification sequence enables the production of high-purity ionic liquid phases, which are free of any contaminants. Although high-purity ionic liquids are very important for catalysis processes, they play an increasingly important role in other application areas, such as polymerization, separation and lubrication sciences.

In one embodiment, the inventive method uses a monophasic system in which an ionic liquid precursor compound is mixed with at least a stoichiometric amount of an inorganic salt to form an ionic liquid. The ionic liquid and an inert liquid are combined to form a monophasic mixture. The monophasic mixture is filtered to yield a filtrate from which the high-purity ionic liquid is recovered. Filtration preferably occurs through a filter aid, most preferably selected from aluminum oxide, Celite, activated carbon, silica gel or a combination thereof.

In a second embodiment, the present method uses a biphasic system in which an ionic liquid and an inert liquid are combined to form a biphasic mixture made up of an aqueous phase and an ionic liquid phase. Then, the aqueous phase and the ionic liquid phase are separated. Next, the ionic liquid phase is filtered to yield a filtrate. The high-purity ionic liquid is recovered from the filtrate.

Furthermore, the present purification procedure can be generally used for the clean-up or recycling of contaminated ionic liquids. In this embodiment, the contaminated ionic liquid is first extracted into a polar extractant to form an extract. Any water traces in the extract are removed, typically by drying the extract over a drying agent, such as magnesium sulfate. Next, the extract is filtered through a filter aid. Lastly, the high-purity ionic liquid is recovered from the filtered extract.

BRIEF DESCRIPTION OF SEVERAL VIEWS OF THE DRAWING

FIG. 1 illustrates ionic liquid preparations using acid treatments that are known in the art.

FIG. 2 shows imidazolium- and pyridinium-based ionic liquids in general.

DETAILED DESCRIPTION OF THE INVENTION

Figure 3:
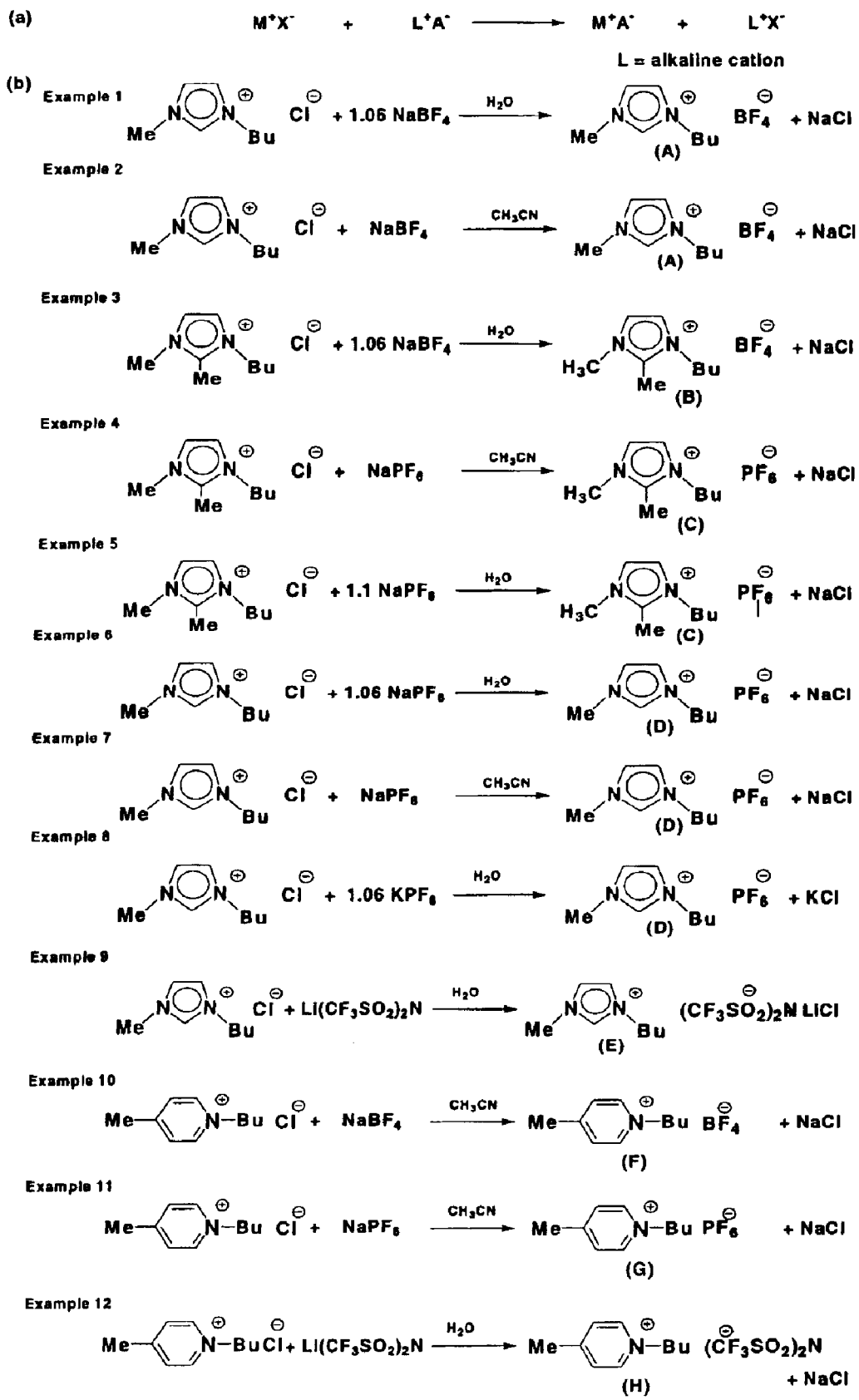
FIG. 3 illustrates the novel high-purity ionic liquid preparation using alkaline salts under different reaction conditions and corresponds with Examples 1–12.

This invention presents a novel process for the preparation of high-purity ionic liquids. These ionic liquids are salts that have melting points at ambient temperatures and can be utilized for a wide variety of applications. These ionic liquids exhibit very low vapor pressure, tunable polarity, and high thermal stability. Depending on the application, the ionic fragments—i.e., anions and cations—can be designed to accommodate the catalysis, separation, or lubrication in the most efficient way. FIG. 2 shows two typical examples of ionic liquids. Although several procedures have been reported for the preparation of ionic liquids, they very often lead to impure products. Depending on the preparation, acid/base traces or halide residues have been found in the resulting ionic liquid products. Based on such impurities, the applications of ionic liquids can be greatly limited.

In the present invention, "high-purity" ionic liquids refers to those having an absence of acid or base traces. Specifically, such ionic liquids exhibit a neutral pH value of 7 and have elemental analysis deviation of less than 0.5 wt % between a calculated elemental analysis and a found elemental analysis for carbon, hydrogen and nitrogen atoms. Elemental analysis measurements and calculations are well known to one skilled in the art.

As is known in the art, the instant ionic liquid has a cationic species and an anionic species. The cationic species is derived from the cationic species of an ionic liquid precursor compound, and the anionic species is derived from the anionic species of an inorganic salt. Preferred ionic liquid precursor compounds comprise quaternary ammonium halides, quaternary phosphonium halides and derivatives thereof. Even more preferred precursor compounds are pyridinium- and imidazolium-derived halides, whereby the preferred cationic species are pyridinium- and imidazolium-derived species. The most preferred cationic species are 1-butyl-3-methyl-imidazolium, 1-butyl-2,3-dimethyl-imidazolium and 1-butyl-4-methyl-pyridinium. The most preferred halide is chloride.

Other possible cationic species of the ionic liquid are selected from, for example, pyrazoles, thiazoles, isothiazoles, azathiozoles, oxothiazoles, oxazines, oxazolines, oxazoboroles, dithiozoles, triazoles, selenozoles, oxaphospholes, pyrroles, boroles, furans, thiophenes, phospholes, pentazoles, indoles, indolines, oxazoles, isooxazoles, isotriazoles, tetrazoles, benzofurans, dibenzofurans, benzothiophenes, dibenzothiophenes, thiadiazoles, pyrimidines, pyrazines, pyridazines, piperazines, piperidines, morpholenes, pyrans, annolines, phthalzines, quinazolines, quinoxalines, quinolines, isoquinolines, thazines, oxazines, and azaannulenes. In addition, acyclic organic systems are also suitable. Examples include, but are not limited to, amines (including amidines, imines and guanidines), phosphines (including phosphinimines), arsines, stibines, ethers, thioethers, selenoethers and mixtures of the above.

Preferred inorganic salts have alkali metal or alkaline-earth metal cationic species and have tetrafluoroborate, hexafluorophosphate, bis-trifluoromethanesulfonimide and derivatives thereof as the anionic species. The most preferred alkali metal cationic species are lithium, sodium and potassium, while the most preferred alkaline-earth metal cationic species are magnesium and calcium.

Other possible anionic species of the ionic liquid include, for example, salts, alkylates and halogenated salts of the Group IB, IIIA, IVA, VA, VIA and VIIA elements of the periodic table, including borates, phosphates, nitrates, sulfates, triflates, halogenated copperates, antimonates, phosphates, phosphites, substituted and unsubstituted carboranes, poly-oxo metallates, substituted (fluorinated, alkylated and arylated) and unsubstituted metalloboranes, substituted and unsubstituted carboxylates and triflates, and mixtures thereof. The periodic table used herein to reference the above-identified groups of elements is from *Hawley's Condensed Chemical Dictionary*, Thirteenth Edition, Richard J. Lewis, Sr., inside front cover (John Wiley & Sons, Inc. 1997). The anionic species may also be a non-coordinating anion, such as tetra[pentafluorophenyl]borane. Examples of some of the above include $BF_4^-$, $PF_6^-$, $CF_3SO_3^-$, $CF_3COO^-$, $SbF_6^-$, $[CuCl_2]^-$, $AsF_6^-$, $SO_4^-$, $CF_3CH_2CH_2COO^-$, $(CF_3SO_2)_3C^-$, $CF_3(CF_2)_3SO_3^-$, $[CF_3SO_2]_2N^-$, or a metal inorganic anion. Most preferably, the anionic species will be selected from $BF_4^-$, $PF_6^-$ and $[CF_3SO_2]_2N^-$.

In one embodiment, the invention is for a method to prepare a high-purity ionic liquid using a monophasic system in which an ionic liquid precursor compound is mixed with at least a stoichiometric amount of an inorganic salt in an inert liquid to form a monophasic mixture. Mixing with at least a stoichiometric amount or a slight excess of the inorganic salt ensures the complete conversion of the halide substrate from the ionic liquid precursor compound and avoids any trace amounts of unreacted halides in the ionic liquids. The preferred inert liquids useful in the instant invention are water, acetonitrile, dichloromethane, chloroform, 1,2-dichloroethane, tetrachloromethane and mixtures thereof, among other inert liquids well known to one skilled in the art. The monophasic mixture formed from this step is an ionic liquid having a cationic species derived from the ionic liquid precursor compound and an anionic species derived from the inorganic salt.

After the mixing step is complete, the monophasic mixture is filtered to initiate the purification process. This filtration step removes any impurities, whether organic or inorganic, from the monophasic mixture to form a filtrate. Filtration preferably occurs through a filter aid. The preferred filter aids are aluminum oxide, Celite, activated carbon, silica gel or a combination thereof. The most preferred filtration step occurs through either a filter aid of activated carbon or aluminum oxide or a combination of the two filter aids. When filtration is finished, the high-purity ionic liquid is recovered from the filtrate. The recovering step is preferably performed by evaporating off volatile components from the filtrate, most preferably at a reduced pressure. Such pressures typically are at about $10^{-2}$ torr. Other recovery methods known to one skilled in the art are also viable, such as an inert gas purge with argon or nitrogen. These filtration steps enable the removal of organic decomposition side-products and help with the separation of any formed inorganic salts.

The most preferred purification procedure using the monophasic system involves using water as the inert liquid and tetrafluoroborate as the anionic species from the inorganic salt. In this process, after a monophasic mixture is formed from the mixing step, it is extracted into a polar extractant to form a polar phase and an aqueous phase. Preferred polar extractants include dichloromethane, 1,2-dichloroethane, tetrachloromethane, chloroform, acetonitrile and mixtures thereof, but other extractants known to one skilled in the art may also be used. After extraction, the polar phase and aqueous phase are separated, most preferably by decanting off whichever one of the polar and aqueous phases has the lighter density. For instance, of the polar extractants identified hereinabove, only acetonitrile has a lighter density than water (density=1 g/L). Thus, when acetonitrile is used as the polar extractant, the lighter top layer would be the polar phase containing the acetonitrile, while the heavier bottom layer would be the aqueous phase. To separate the phases, the lighter polar phase would be decanted off. On the other hand, when either one of dichloromethane, 1,2-dichloroethane, tetrachloromethane or chloroform is used as the polar extractant, the top layer would be the aqueous phase, while the bottom layer would be the polar phase containing the chloroform. In this case, the separation step would occur by decanting off the lighter aqueous phase. Other separation methods are known to one skilled in the art.

Next, before the filtration step commences, any remaining water in the polar phase is removed to form a dried monophasic mixture. The preferred water removal step includes drying the polar phase over a drying agent, the most preferred of which is magnesium sulfate, but other drying agents known to one skilled in the art may also be used. After the water removal step, the same filtration and recovery steps disclosed hereinabove are utilized to purify the ionic liquid. Examples 1 and 3 exemplify this most preferred embodiment.

In another embodiment, the instant invention is for a method to prepare a high-purity ionic liquid using a biphasic system in which an ionic liquid and an inert liquid are combined to form a biphasic mixture made up of an aqueous phase and an ionic liquid phase. The next step requires separating the aqueous phase and the ionic liquid phase, typically by the decanting procedure described hereinabove. However, in this case, the ionic liquid phase will usually have a higher density than the aqueous phase, so the aqueous phase will be the top layer to be decanted off. Other separation processes are known to one skilled in the art. After the aqueous and ionic liquid phases are separated, the latter is filtered using the methods specified hereinabove to yield a filtrate. Then, the high-purity ionic liquid is recovered from the filtrate, preferably by evaporating the filtrate in the manner specified hereinabove.

In a manner similar to the monophasic system, this embodiment of a biphasic system comprises mixing an ionic liquid precursor compound with at least a stoichiometric amount of an inorganic salt in an inert liquid to form the biphasic mixture. As stated above, the cationic species of the ionic liquid is derived from the precursor compound and the anionic species of the ionic liquid is derived from the inorganic salt. However, in this embodiment, the anionic species is optimally either hexafluorophosphate or bis-trifluoromethanesulfonimide and the inert liquid is optimally water.

In a preferred embodiment using the biphasic system, a dissolving step is added after the separating step in which ionic liquid phase is dissolved (or diluted). The dissolving step is preferably performed using a polar extractant. The polar extractant used here can be the same as those listed hereinabove. After the dissolving step is completed, any remaining water in the ionic liquid phase is removed in the manner specified hereinabove. Then, the filtering and recovering steps can be performed to obtain the high-purity ionic liquid.

In another preferred embodiment using the biphasic system, an extracting step is added after the mixing step whereby the biphasic mixture is extracted into a polar extractant to form an aqueous phase and a polar phase. The polar phase contains the ionic liquid phase. The polar extractants useful in this embodiment are the same as those disclosed hereinabove. Next, the polar phase is separated from the aqueous phase, typically by the decanting procedure described hereinabove. Then, any remaining water from the polar phase is removed to form a dried polar phase. The removing water step preferably involves drying the polar phase over a drying agent in the manner specified hereinabove. The dried polar phase is filtered to form a filtrate in the manner specified hereinabove. And the high-purity ionic liquid is recovered from the filtrate in the manner specified above.

In yet another embodiment, the present invention is directed to a method for purifying a contaminated ionic liquid to form a high-purity ionic liquid having the characteristics defined above. The first step involves extracting the contaminated ionic liquid into a polar extractant to form an extract containing the ionic liquid. The second step involves removing any water traces from the extract. The third step involves filtering the extract. Lastly, the high-purity ionic liquid is recovered from the extract. The polar extractant and other steps described in this embodiment are the same as those disclosed hereinabove for the other embodiments.

The reactions disclosed herein are preferably performed at room temperature and atmospheric pressure. The duration of the reactions is dependent upon the inorganic salt and inert liquid utilized.

The invention is further described in the following non-limiting examples.

EXAMPLES

Example 1

Synthesis of 1-Butyl-3-methyl-imidazolium Tetrafluoroborate (A)

The compound 1-(butyl)-3-(methyl)-imidazolium chloride (0.54 mol, 94.6 g) and sodium tetrafluoroborate (1.06 eq.) (0.57 mol, 62.5 g) were dissolved in distilled water (0.25 L). After 15 hours, the reaction mixture containing the ionic liquid 1-(butyl)-3-(methyl)-imidazolium tetrafluoroborate (compound A) was treated with dichloromethane. The resulting mixture was stirred for approximately an additional 10 minutes. After the stirring was stopped, the phases separated into the polar phase and the aqueous phase. The polar phase was separated from the aqueous phase by decantation. This extraction procedure was repeated 3 times using dichloromethane (3×0.2 L) as the polar extractant. The combined polar phases were dried over magnesium sulfate and filtered through a filter aid combination made up of aluminum oxide and activated carbon. After the removal of the volatile components under reduced pressure ($10^{-2}$ torr), compound A was recovered as a clear, colorless liquid in 73% yield (0.39 mol, 89.1 g); $^1$H NMR (CD$_2$Cl$_2$) δ=0.94 (m, 3H, CH$_2$—C$\underline{H}_3$), 1.34 (m, 2H), C$\underline{H}_2$—CH$_3$), 1.85 (m, 2H, C$\underline{H}_2$—CH$_2$—CH$_3$), 3.92 (s, 3H, N$_1$—C$\underline{H}_3$), 4.18 (m, 2H, N$_3$—C$\underline{H}_2$), 7.42 (s, 2H, C4I—$\underline{H}$, C5I—$\underline{H}$), 8.71 (s, 1H, C2I—$\underline{H}$) ppm; $^{13}$C-NMR (CD$_2$Cl$_2$) δ=13.43 (CH$_2$—$\underline{C}$H$_3$), 19.68 ($\underline{C}$H$_2$—CH$_3$), 32.24 ($\underline{C}$H$_2$—CH$_2$—CH$_3$), 36.46 (N1-$\underline{C}$H$_3$), 50.11 (N3-$\underline{C}$H$_2$), 122.77 ($\underline{C}$4I), 124.16 ($\underline{C}$5I), 136.61 ($\underline{C}$2I) ppm; elemental analysis (%) calculated for C$_8$H$_{15}$N$_2$BF$_4$: C, 42.51; H, 6.69; N, 12.39; found C, 42.66; H, 7.12; N, 12.49.

Example 2

Synthesis of 1-Butyl-3-methyl-imidazolium Tetrafluoroborate (A)

The compound 1-(butyl)-3-(methyl)-imidazolium chloride (1.3 mol, 230.0 g) and sodium tetrafluoroborate (1.3 mol, 144.6 g) were stirred as a slurry in acetonitrile (0.5 L) at room temperature. After a reaction time of 4 days, the resulting mixture containing the ionic liquid 1-(butyl)-3-(methyl)-imidazolium tetrafluoroborate (compound A) was filtered through a Celite filter aid. The clear liquid was freed from the volatile components by evaporation under reduced pressure ($10^{-2}$ torr). Compound A was recovered as a clear, colorless liquid in 90% yield (1.2 mol, 268.6 g). $^1$H NMR (CD$_3$CN) δ=0.93 (m, 3H, CH$_2$—C$\underline{H}_3$), 1.31 (m, 2H, CH$_2$—CH$_3$), 1.79 (m, 2H, C$\underline{H}$2-CH$_2$—CH$_3$), 3.84 (s, 3H, N$_1$—C$\underline{H}_3$), 4.15 (m, 2H, N$_3$—C$\underline{H}_2$), 7.39 (s, 1H, C5I—$\underline{H}$), 7.42 (s, 1H, C4I—$\underline{H}$), 8.57 (s, 1H, C2I—$\underline{H}$) ppm; $^{13}$C-NMR (CD$_3$CN) δ=13.64 (CH$_2$—$\underline{C}$H$_3$), 19.92 ($\underline{C}$H$_2$—CH$_3$), 32.54 ($\underline{C}$H$_2$—CH$_2$—CH$_3$), 36.71 (N1-$\underline{C}$H$_3$), 50.18 (N3-CH2), 123.18 (C4I), 124.56 (C5I), 137.08 (C2I) ppm; elemental analysis (%) calculated for C$_8$H$_{15}$N$_2$BF$_4$: C, 42.51; H, 6.69; N, 12.39; found C, 42.58; H, 6.98; N, 12.34.

Example 3

Synthesis of 1-Butyl-2,3-dimethyl-imidazolium Tetrafluoroborate (B)

The compound 1-(butyl)-2,3-(dimethyl)-imidazolium chloride (0.30 mol, 56.6 g) was dissolved in distilled water (0.4 L) to give a hazy amber colored solution. After stirring for 15 hours, the clear amber colored solution was treated with sodium tetrafluoroborate (0.33 mol, 36.2 g) at 45° C. The mixture was stirred for 2 days and then treated with dichloromethane. The resulting mixture containing the ionic liquid 1-(butyl)-2,3-(dimethyl)-imidazolium tetrafluoroborate (compound B) was stirred for approximately an additional hour. After the stirring was stopped, the phases separated into the polar phase and the aqueous phase. The aqueous phase was separated from the polar phase by decantation. This extraction procedure was repeated 3 times using dichloromethane (3×0.2 L) as the polar extractant. The combined polar phases were dried over magnesium sulfate and filtered through a filter aid combination of aluminum oxide and activated carbon. The filtrate was freed from the volatile components under reduced pressure ($10^{-2}$ torr) and compound B was isolated as a clear yellow liquid in 73% yield (0.22 mol, 54.0 g). $^1$H NMR (CD$_2$Cl$_2$) δ=0.96 (m, 3H, CH$_2$—C$\underline{H}_3$), 1.38 (m, 2H, C$\underline{H}_2$—CH$_3$), 1.77 (m, 2H, C$\underline{H}_2$—CH$_2$—CH$_3$), 2.59 (s, 3H, C3I—C$\underline{H}_3$), 3.79 (s, 3H, N$_1$—C$\underline{H}_3$), 4.07 (m, 2H, N$_3$—C$\underline{H}_2$), 7.27 (s, 1H, C5I—$\underline{H}$), 7.30 (s, 1H, C4I—$\underline{H}$) ppm; $^{13}$C-NMR (CD$_2$Cl$_2$) δ=9.95 (CH$_2$—$\underline{C}$H$_3$), 13.84 ($\underline{C}$H$_2$—CH$_3$), 20.03 ($\underline{C}$H$_2$—CH$_2$—CH$_3$), 32.14 (C2I—$\underline{C}$H$_3$), 35.59 (N1-$\underline{C}$H$_3$), 49.95 (N3-$\underline{C}$H$_2$), 121.42 ($\underline{C}$4I), 123.07 ($\underline{C}$5I), 144.45 ($\underline{C}$2I) ppm; elemental analysis (%) calculated for C$_9$H$_{17}$N$_2$BF$_4$: C, 45.03; H, 7.14; N, 11.67; found C, 44.87; H, 7.44; N, 11.54.

Example 4

Synthesis of 1-Butyl-2,3-dimethyl-imidazolium Hexafluorophosphate (C)

The compound 1-(butyl)-2,3-(dimethyl)-imidazolium chloride (1.1 mol, 213.3 g) and sodium hexafluorophosphate (1.1 mol, 189.9 g) were stirred as a slurry in acetonitrile (0.5 L) at room temperature. After a reaction time of 4 days, the resulting mixture containing the ionic liquid 1-(butyl)-2,3-(dimethyl)-imidazolium hexafluorophosphate (compound C) was filtered through a Celite filter aid. The clear amber colored liquid was freed from the volatile components by evaporation under reduced pressure ($10^{-2}$ torr). Compound C was recovered as a yellow colorless viscous liquid in 91% yield (1.0 mol, 305.0 g). $^1$H NMR (CD$_3$CN) δ=0.94 (m, 3H, CH$_2$—C$\underline{H}_3$), 1.33 (m, 2H, C$\underline{H}_2$—CH$_3$), 1.74 (m, 2H, C$\underline{H}_2$—CH$_2$—CH$_3$), 2.50 (s, 3H, C3I—C$\underline{H}_3$), 3.70 (s, 3H, N$_1$—C$\underline{H}_3$), 4.03 (m, 2H, N$_3$—C$\underline{H}_2$), 7.24 (s, 1H, C5I—$\underline{H}$), 7.25 (s, 1H, C4I—$\underline{H}$) ppm; $^{13}$C-NMR (CD$_3$CN) δ=9.95 (CH$_2$—$\underline{C}$H$_3$), 13.67 ($\underline{C}$H$_2$—CH$_3$), 20.07 ($\underline{C}$H$_2$—CH$_2$—CH$_3$), 32.19 (C2I—$\underline{C}$H$_3$), 35.67 (N1-$\underline{C}$H$_3$), 49.01 (N3-$\underline{C}$H$_2$), 121.73 ($\underline{C}$4I), 123.22 ($\underline{C}$5I), 145.38 ($\underline{C}$2I) ppm; elemental analysis (%) calculated for C$_9$H$_{17}$N$_2$PF$_6$: C, 36.25; H, 5.75; N, 9.39; found C, 35.70; H, 5.92; N, 9.35.

Example 5

Synthesis of 1-Butyl-2,3-dimethyl-imidazolium Hexafluorophosphate (C)

The compound 1-(butyl)-2,3-(dimethyl)-imidazolium chloride (0.30 mol, 56.6 g) was dissolved in distilled water (0.4 L) to give a hazy amber-colored solution. After stirring for 2 hours, sodium hexafluorophosphate (0.33 mol, 55.4 g) was added as a solid at 25° C. Following the addition, the temperature was slightly increased to avoid solidification of the formed product. The mixture containing the ionic liquid 1-(butyl)-2,3-(dimethyl)-imidazolium hexafluorophosphate (compound C) was stirred for 15 hours and then treated with dichloromethane (0.3 L). The resulting mixture was stirred for approximately an additional hour. After the stirring was stopped, the phases separated into the polar phase and the aqueous phase. The aqueous phase was separated from the polar phase by decantation. This extraction procedure was repeated 3 times using dichloromethane (3×0.2 L) as the polar extractant. The resulting combined amber-colored polar phases were dried over magnesium sulfate and filtered through a filter aid combination of aluminum oxide and activated carbon. The filtrate was freed from the volatile components under reduced pressure ($10^{-2}$ torr) and compound C was isolated as a yellow-colored viscous liquid in 55% yield (0.16 mol, 49.0 g). $^1$H NMR (CD$_3$CN) δ=0.94 (m, 3H, CH$_2$—C$\underline{H}_3$), 1.33 (m, 2H, C$\underline{H}_2$—CH$_3$), 1.74 (m, 2H, C$\underline{H}_2$—CH$_2$—CH$_3$), 2.50 (s, 3H, C3I—C$\underline{H}_3$), 3.70 (s, 3H, N$_1$—C$\underline{H}_3$), 4.03 (m, 2H, N$_3$—C$\underline{H}_2$), 7.24 (s, 1H, C5I—$\underline{H}$), 7.25 (s, 1H, C4I—$\underline{H}$) ppm; $^{13}$C-NMR (CD$_3$CN) δ=9.95 (CH$_2$—$\underline{C}$H$_3$), 13.67 ($\underline{C}$H$_2$—CH$_3$), 20.07 ($\underline{C}$H$_2$—CH$_2$—CH$_3$), 32.19 (C2I—$\underline{C}$H$_3$), 35.67 (N1-$\underline{C}$H$_3$), 49.01 (N3-$\underline{C}$H$_2$), 121.73 ($\underline{C}$4I), 123.22 ($\underline{C}$5I), 145.38 ($\underline{C}$2I) ppm; elemental analysis (%) calculated for C$_9$H$_{17}$N$_2$PF$_6$: C, 36.25; H, 5.75; N, 9.39; found C, 36.27; H, 5.83; N, 9.36.

A comparison was performed between the commercially available ionic liquid 1-butyl-2,3-dimethyl-imidazolium hexafluorophosphate obtained from Sachem, Inc. (also available from Aldrich Chem. Co. and Strem Chem. Co.) and the same ionic liquid prepared according to Example 5 (compound C). The litmus indicator showed that the Sachem material turned red and, thus, contained acidic traces. Conversely, the preparation according to Example 5 did not change colors, meaning it was neutral.

Example 6

Synthesis of 1-Butyl-3-methyl-imidazolium Hexafluorophosphate (D)

The compound 1-(butyl)-3-(methyl)-imidazolium chloride (0.33 mol, 57.5 g) and sodium hexafluorophosphate (1.05 equivalents) (0.35 mol, 60.3 g) were dissolved in distilled water (0.25 L). After stirring for 18 hours, an ionic liquid phase consisting of 1-(butyl)-3-(methyl)-imidazolium hexafluorophosphate (compound D) was formed. The aqueous phase and the ionic liquid phase were separated and the ionic liquid phase was washed with distilled water (3×0.25 L). The ionic liquid phase was dissolved with acetonitrile (0.1 L) and dried over magnesium sulfate. After filtration through a Celite filter aid, the volatile components were removed under reduced pressure ($10^{-2}$ torr). Compound D was obtained as a clear, colorless liquid in 70% yield (0.23 mol, 66.0 g). $^1$H NMR ($CD_2Cl_2$) δ=0.93 (m, 3H, $CH_2$—C$\underline{H}_3$), 1.34 (m, 2H, C$\underline{H}_2$—$CH_3$), 1.85 (m, 2H, C$\underline{H}_2$—$CH_2$—$CH_3$), 3.89 (s, 3H, $N_1$—C$\underline{H}_3$), 4.13 (m, 2H, $N_3$—C$\underline{H}_2$), 7.34 (s, 1H, C4I—$\underline{H}$), 7.35 (s, 1H, C5I—$\underline{H}$), 8.42 (s, 1H, C2I—$\underline{H}$) ppm; $^{13}$C-NMR ($CD_2Cl_2$) δ=13.37 ($CH_2$—$\underline{C}H_3$), 19.63 ($\underline{C}H_2$—$CH_3$), 32.09 ($\underline{C}H_2$—$CH_2$—$CH_3$), 36.39 (N1-$\underline{C}H_3$), 50.13 (N3-$\underline{C}H_2$), 122.71 ($\underline{C}4I$), 124.03 ($\underline{C}5I$), 136.04 ($\underline{C}2I$) ppm; elemental analysis (%) calculated for $C_8H_{15}N_2PF_6$: C, 33.81; H, 5.32; N, 9.86; found C, 34.37; H, 5.66; N, 10.25.

Example 7

Synthesis of 1-Butyl-3-methyl-imidazolium Hexafluorophosphate (D)

The compound 1-(butyl)-3-(methyl)-imidazolium chloride (0.51 mol, 89.5 g) and sodium hexafluorophosphate (0.51 mol, 86.0 g) were dissolved in acetonitrile (0.2 L). After stirring for 6 days, the reaction mixture containing the ionic liquid 1-(butyl)-3-(methyl)-imidazolium hexafluorophosphate (compound D) was filtered through a Celite filter aid. The resulting filtrate was dried over magnesium sulfate and filtered through a Celite filter aid. The volatile components were removed by evaporation under reduced pressure ($10^{-2}$ torr). Compound D was recovered as a clear, colorless liquid in 92% yield (0.47 mol, 135.5 g). $^1$H NMR ($CD_3CN$) δ=0.94 (m, 3H, $CH_2$—C$\underline{H}_3$), 1.35 (m, 2H, C$\underline{H}_2CH_3$), 1.88 (m, 2H, C$\underline{H}_2$—$CH_2$—$CH_3$), 3.93 (s, 3H, $N_1$—C$\underline{H}_3$), 4.23 (m, 2H, $N_3$—C$\underline{H}_2$), 7.44 (s, 1H, C4I—$\underline{H}$), 7.48 (s, 1H, C5I—$\underline{H}$), 8.50 (s, 1H, C2I—$\underline{H}$) ppm; $^{13}$C-NMR ($CD_3CN$) δ=13.51 ($CH_2$—$\underline{C}H_3$), 19.79 ($\underline{C}H_2$—$CH_3$), 32.34 ($\underline{C}H_2$—$CH_2$—$CH_3$), 36.44 (N1-$\underline{C}H_3$), 50.17 (N3-$\underline{C}H_2$), 122.96 ($\underline{C}4I$), 124.32 ($\underline{C}5I$), 136.93 ($\underline{C}2I$) ppm; elemental analysis (%) calculated for $C_8H_{15}N_2PF_6$: C, 33.81; H, 5.32; N, 9.86; found C, 33.80; H, 5.19; N, 10.54.

Example 8

Synthesis of 1-Butyl-3-methyl-imidazolium Hexafluorophosphate (D)

The compound 1-(butyl)-3-(methyl)-imidazolium chloride (1.0 mol, 174.6 g) and potassium hexafluorophosphate (1.02 equivalents) (1.02 mol, 187.8 g) were dissolved in distilled water (0.4 L). After stirring for 5 days, an ionic liquid phase containing 1-(butyl)-3-(methyl)-imidazolium hexafluorophosphate (compound D) was formed. The resulting reaction mixture was treated with dichloromethane. This biphasic mixture was stirred for approximately an additional hour. After the stirring was stopped, the phases separated into the polar phase and the aqueous phase. The aqueous phase was separated from the polar phase by decantation. This extraction procedure was repeated 3 times using dichloromethane (3×0.2 L) as the polar extractant. The combined polar phases were dried over magnesium sulfate and filtered through a filter aid combination of Celite and activated carbon. The volatile components were removed under reduced pressure ($10^{-2}$ torr) to recover compound D as a clear, colorless liquid in 80% yield (0.80 mol, 226.3 g). $^1$H NMR ($CD_2Cl_2$) δ=0.94 (m, 3H, $CH_2$—C$\underline{H}_3$), 1.34 (m, 2H, C$\underline{H}_2$—$CH_3$), 1.85 (m, 2H, C$\underline{H}_2$—$CH_2$—$CH_3$), 3.89 (s, 3H, $N_1$—C$\underline{H}_3$), 4.12 (m, 2H, $N_3$—C$\underline{H}_2$), 7.32 (s, 2H, C4I—$\underline{H}$, C5I—$\underline{H}$), 8.42 (s, 1H, C2I—$\underline{H}$) ppm; $^{13}$C-NMR ($CD_2Cl_2$) δ=13.50 ($CH_2$—$\underline{C}H_3$), 19.79 ($\underline{C}H_2$—$CH_3$), 32.24 ($\underline{C}H_2$—$CH_2$—$CH_3$), 36.63 (N1-$\underline{C}H_3$), 50.34 (N3-$\underline{C}H_2$), 122.77 ($\underline{C}4I$), 124.14 ($\underline{C}5I$), 136.04 ($\underline{C}2I$) ppm; elemental analysis (%) calculated for $C_8H_{15}N_2PF_6$: C, 33.81; H, 5.32; N, 9.86; found C, 33.92; H, 5.64; N, 9.72.

Example 9

Synthesis of 1-Butyl-3-methyl-imidazolium Bis-trifluoromethanesulfonimide (E)

The compound 1-(butyl)-3-(methyl)-imidazolium chloride (0.8 mol, 139.7 g) was dissolved in distilled water (0.5 L). After stirring for 1 hour, the solution was treated with lithium bis-trifluoromethanesulfonimide (0.8 mol, 229.7 g) at room temperature. The color of the reaction mixture turned white and a second liquid phase consisting of the ionic liquid 1-(butyl)-3-(methyl)-imidazolium bis-trifluoromethanesulfonimide (compound E) started to form. The aqueous phase and the ionic liquid phase were separated and the ionic liquid phase was dissolved in dichloromethane (0.1 L). The solution containing the ionic liquid phase was treated with magnesium sulfate and filtered through an aluminum oxide filter aid. After the evaporation of the volatile components, compound E was isolated in 90% yield (330.6 g, 0.72 mol). $^1$H NMR ($CD_2Cl_2$) δ=0.96 (m, 3H, $CH_2$—C$\underline{H}_3$), 1.35 (m, 2H, C$\underline{H}_2$—$CH_3$), 1.85 (m, 2H, C$\underline{H}_2$—$CH_2$—$CH_3$), 3.92 (s, 3H, $N_1$—C$\underline{H}_3$), 4.16 (m, 2H, $N_3$—C$\underline{H}_2$), 7.32 (s, 2H, C4,5I—$\underline{H}$), 8.62 (s, 1H, (s, 1H, C2I—$\underline{H}$) ppm; $^{13}$C-NMR ($CD_2Cl_2$) δ=13.30 ($CH_2$—$\underline{C}H_3$), 19.41 ($\underline{C}H_2$—$CH_3$), 31.94 ($\underline{C}H_2$—$CH_2$—$CH_3$), 36.37 (N1-$\underline{C}H_3$), 50.08 (N3-$\underline{C}H_2$), 122.43 ($\underline{C}4I$), 123.78 ($\underline{C}5I$), 135.83 ($\underline{C}2I$) ppm; elemental analysis (%) calculated for $C_{10}H_{15}N_3F_6O_4S_2$: C, 28.64; H, 3.61; N, 10.02; found C, 28.75; H, 3.63; N, 10.03.

Example 10

Synthesis of 1-Butyl-4-methyl-pyridinium Tetrafluoroborate (F)

The compound 1-(butyl)-4-(methyl)-pyridinium chloride (0.43 mol, 80.0 g) was dissolved in acetonitrile (0.7 L) and treated with sodium tetrafluoroborate (0.43 mol, 47.3 g) at room temperature. After a reaction time of 5 days, the resulting mixture containing the ionic liquid 1-(butyl)-4-(methyl)-pyridinium tetrafluoroborate (compound F) was separated by filtration through a filter aid combination of Celite and activated carbon. The clear amber colored liquid was freed from the volatile components by evaporation under reduced pressure ($10^{-2}$ torr). Compound F was recovered as a yellow liquid in 86% yield (0.37 mol, 88.0 g). $^1$H NMR ($CD_3CN$) δ=0.94 (m, 3H, $CH_2$—C$\underline{H}_3$), 1.34 (m, 2H, C$\underline{H}_2$—$CH_3$), 1.92 (m, 2H, C$\underline{H}_2$—$CH_2$—$CH_3$), 2.63 (s, 3H, py-C$\underline{H}_3$), 4.48 (m, 2H, N—C$\underline{H}_2$), 7.84 (m, 2H, C$\underline{H}$—N—C$\underline{H}$), 8.58 (m, 2H, C$\underline{H}$—CH—N—CH—C$\underline{H}$) ppm; $^{13}$C-NMR ($CD_3CN$) δ=13.61 ($CH_2$—$\underline{C}H_3$), 19.83 ($\underline{C}H_2$—$CH_3$), 22.04 (py-$\underline{C}H_3$), 33.61 ($\underline{C}H_2$—$CH_2$—$CH_3$), 61.66 $\underline{C}H_2$—$CH_2$—$CH_2$—$CH_3$), 129.62 ($\underline{C}H$—N—$\underline{C}H$), 144.32 ($\underline{C}H$—CH—N—CH—$\underline{C}H$), 160.72 ($\underline{C}$4-py) ppm; elemental analysis (%) calculated for $C_{10}H_{16}NBF_4$: C, 50.67; H, 6.80; N, 5.91; found C, 50.39; H, 6.62; N, 5.92.

Example 11

Synthesis of 1-Butyl-4-methyl-pyridinium Hexafluorophosphate (G)

The compound 1-(butyl)-4-(methyl)-pyridinium chloride (1.0 mol, 185.6 g) was dissolved in acetonitrile (0.8 L) and treated with sodium hexafluorophosphate (1.0 mol, 168.0 g) at room temperature. After a reaction time of 5 days, the resulting mixture containing the ionic liquid 1-(butyl)-4-(methyl)-pyridinium hexafluorophosphate (compound G) was filtered through a filter aid combination of Celite and activated carbon. The clear amber colored liquid was freed from the volatile components by evaporation under reduced pressure ($10^{-2}$ torr). Compound G was obtained as an amber colored liquid in 77% yield (0.77 mol, 226.0 g). $^1$H NMR (CD$_2$Cl$_2$) δ=0.96 (m, 3H, CH$_2$—CH$_3$), 1.36 (m, 2H, CH$_2$—CH$_3$), 1.94 (m, 2H, CH$_2$—CH$_2$—CH$_3$), 2.66 (s, 3H, py-CH$_3$), 4.49 (m, 2H, N—CH$_2$), 7.81 (m, 2H, CH—N—CH), 8.52 (m, 2H, CH—CH—N—CH—CH) ppm; $^{13}$C-NMR (CD$_2$Cl$_2$) δ=13.41 (CH$_2$—CH$_3$), 19.59 (CH$_2$—CH$_3$), 22.24 (py-CH$_3$), 33.43 (CH$_2$—CH$_2$—CH$_3$), 61.82 CH$_2$—CH$_2$—CH$_2$—CH$_3$), 129.43 (CH—N—CH), 143.42 (CH—CH—N—CH—CH), 160.37 (C4-py) ppm; elemental analysis (%) calculated for C$_{10}$H$_{16}$NPF$_6$: C, 40.69; H, 5.46; N, 4.74; found C, 40.73; H, 5.53; N, 4.70.

Example 12

Synthesis of 1-Butyl-4-methyl-pyridinium Bis-trifluoromethane-sulfonimide (H)

The compound 1-(butyl)-4-(methyl)-pyridinium chloride (0.5 mol, 92.8 g) and lithium bis-trifluoromethanesulfonimide (0.5 mol, 143.6 g) were dissolved in distilled water (0.3 L) and stirred for 15 hours at room temperature. During the course of the reaction, an ionic liquid phase consisting of 1-(butyl)-4-(methyl)-pyridinium bis-trifluoromethanesulfonimide (compound H) formed at the bottom of the reaction vessel. The aqueous phase was separated from the slightly orange-colored ionic liquid phase, and the ionic liquid phase was dissolved in dichloromethane and dried over magnesium sulfate. The resulting solution containing the ionic liquid was filtered through an activated carbon filter aid before the volatile components were evaporated under reduced pressure ($10^{-2}$ torr). Compound H was recovered as a yellow-colored liquid in 92% yield (0.46 mol, 198.0 g). $^1$H NMR (CD$_2$Cl$_2$) δ=0.97 (m, 3H, CH$_2$—CH$_3$), 1.37 (m, 2H, CH$_2$—CH$_3$), 1.95 (m, 2H, CH$_2$—CH$_2$—CH$_3$), 2.67 (s, 3H, py-CH$_3$), 4.49 (m, 2H, N—CH$_2$), 7.81 (m, 2H, CH—N—CH), 8.54 (m, 2H, CH—CH—N—CH—CH) ppm; $^{13}$C-NMR (CD$_2$Cl$_2$) δ=13.36 (CH$_2$—CH$_3$), 19.64 (CH$_2$—CH$_3$), 22.31 (py-CH$_3$), 33.52 (CH$_2$—CH$_2$—CH$_3$), 61.92 CH$_2$—CH$_2$—CH$_2$—CH$_3$), 120.34 (q, 2C, CF$_3$—), 129.54 (CH—N—CH), 143.51 (CH—CH—N—CH—CH), 160.49 (C4-py) ppm; elemental analysis (%) calculated for C$_{12}$H$_{16}$N$_2$F$_6$S$_2$: C, 33.49; H, 3.75; N, 6.51; found C, 33.43; H, 3.75; N 6.57.

$^1$H- and $^{13}$C-NMR, elemental analysis, and HPLC analysis have confirmed the purity of all the ionic liquids prepared by the instant method. None of the high-purity ionic liquids showed any residual acid/base or halide contamination. Consequently, the present ionic liquids did not undergo any acid initiated decomposition and can be used as reaction media for catalysis (hydroformylation and hydrogenation reactions, etc.) and in other applications, such as polymerization, separation and lubrication sciences.

The invention having been thus described, it will be obvious that the same may be varied in many ways without departing from the spirit and scope of the invention, as defined by the following claims.

What is claimed is:

1. A method for preparing a high-purity ionic liquid having a pH value of 7 and an elemental analysis deviation of less than 0.5 wt % between a calculated elemental analysis and a found elemental analysis for each of carbon, hydrogen and nitrogen, the method comprising forming a monophasic or biphasic mixture of an ionic liquid and an inert liquid, wherein the ionic liquid comprises a cationic species and an anionic species wherein the anionic species is selected from the group consisting of tetrafluoroborate, hexafluorophosphate, bis-trifluoromethanesulfonimide and derivatives thereof, wherein the biphasic mixture comprises an aqueous phase and an ionic liquid phase; and (a) when the monophasic mixture is formed:
  (i) filtering the monophasic mixture to yield a filtrate; and
  (ii) recovering the ionic liquid from the filtrate; and
(b) when the biphasic mixture is formed:
  (i) separating the ionic liquid phase from the aqueous phase;
  (ii) filtering the ionic liquid phase to yield a filtrate; and
  (iii) recovering the ionic liquid from the filtrate.

2. The method of claim 1 wherein the inert liquid is selected from the group consisting of water, acetonitrile, dichloromethane, chloroform, 1,2-dichloroethane, tetrachloromethane and mixtures thereof.

3. The method of claim 1 wherein the filtering step comprises filtering the monophasic mixture or the ionic liquid phase through a filter aid comprising at least one of aluminum oxide, Celite, activated carbon and silica gel.

4. The method of claim 1 wherein the filtering step comprises filtering the monophasic mixture or the ionic liquid phase through a filter aid comprising activated carbon.

5. The method of claim 1 wherein the filtering step comprises filtering the monophasic mixture or the ionic liquid phase through a filter aid comprising aluminum oxide.

6. The method of claim 1 wherein the filtering step comprises filtering the monophasic mixture or the ionic liquid phase through a combination of filter aids comprising activated carbon and aluminum oxide.

7. The method of claim 1 wherein the separating step comprises decanting off the aqueous phase from the ionic liquid phase.

8. The method of claim 1 wherein the recovering step comprises evaporating off volatile components from the filtrate to recover the ionic liquid.

9. The method of claim 8 wherein the evaporating step comprises evaporating off the volatile components from the filtrate at a reduced pressure to recover the ionic liquid.

10. The method of claim 1 wherein the forming the monophasic mixture step comprises mixing an ionic liquid precursor compound with at least a stoichiometric amount of an inorganic salt in the inert liquid to form the monophasic mixture, wherein a cationic species of the ionic liquid is derived from the precursor compound and an anionic species of the ionic liquid is derived from the inorganic salt.

11. The method of claim 10 wherein the inert liquid comprises water and the anionic species comprises tetrafluoroborate, the method further comprising the steps of:

(a) extracting the monophasic mixture into a polar extractant to form a polar phase and an aqueous phase, the extracting step occurring after the mixing step;
(b) separating the polar phase from the aqueous phase; and
(c) removing any remaining water from the polar phase to form a dried monophasic mixture, the removing step occurring before the filtering step.

12. The method of claim 11 wherein the polar extractant is selected from the group consisting of dichloromethane, 1,2-dichloroethane, tetrachloromethane, chloroform, acetonitrile and mixtures thereof.

13. The method of claim 11 wherein the separating step comprises decanting off the less dense phase selected from one of the polar phase and the aqueous phase.

14. The method of claim 11 wherein the removing step comprises drying the polar phase over a drying agent to form a dried monophasic mixture.

15. The method of claim 14 wherein the drying agent comprises magnesium sulfate.

16. The method of claim 1 wherein the forming the biphasic mixture step comprises mixing an ionic liquid precursor compound with at least a stoichiometric amount of a hexafluorophosphate or bis-trifluoromethanesulfonimide salt in water to form the biphasic mixture having an aqueous phase and an ionic liquid phase, wherein a cationic species of the ionic liquid is derived from the precursor compound and an anionic species of the ionic liquid is derived from the hexafluorophosphate or bis-trifluoromethanesulfonimide salt.

17. The method of claim 16 further comprising the steps of:
(a) dissolving the ionic liquid phase, the dissolving step occurring after the separating step; and
(b) removing any remaining water from the ionic liquid phase, the removing step occurring after the dissolving step and before the filtering step.

18. The method of claim 17 wherein the dissolving step comprises dissolving the ionic liquid phase with a polar extractant selected from the group consisting of dichloromethane, 1,2-dichloroethane, tetrachloromethane, chloroform, acetonitrile and mixtures thereof.

19. The method of claim 17 wherein the removing step comprises drying the ionic liquid phase over a drying agent.

20. The method of claim 19 wherein the drying agent comprises magnesium sulfate.

21. The method of claim 16 further comprising the steps of:
(a) extracting the biphasic mixture into a polar extractant to form an aqueous phase and a polar phase comprising the ionic liquid phase, the extracting step occurring after the mixing step and before the separating step, wherein the separating step comprises separating the polar phase from the aqueous phase; and
(b) removing any remaining water from the polar phase to form a dried polar phase, the removing step occurring after the separating step and before the filtering step.

22. The method of claim 21 wherein the polar extractant is selected from the group consisting of dichloromethane, 1,2-dichloroethane, tetrachloromethane, chloroform, acetonitrile and mixtures thereof.

23. The method of claim 21 wherein the separating step comprises decanting off the less dense phase selected from the group consisting of the polar phase and the aqueous phase.

24. The method of claim 21 wherein the removing step comprises drying the extract over a drying agent to form a dried polar phase.

25. The method of claim 23 wherein the drying agent comprises magnesium sulfate.

26. The method of claim 10 or 16 wherein the ionic liquid precursor compound is selected from the group consisting of quaternary ammonium halides, quaternary phosphonium halides and derivatives thereof.

27. The method of claim 26 wherein the ionic liquid precursor compound comprises a cationic species and an anionic species, wherein the cationic species thereof is selected from the group consisting of a pyridinium-derived species and an imidazolium-derived species, and further wherein the anionic species thereof comprises a halide.

28. The method of claim 27 wherein the pyridinium-derived species comprises 1-butyl-4-methyl-pyridinium.

29. The method of claim 27 wherein the imidazolium-derived species is selected from the group consisting of 1-butyl-3-methyl-imidazolium and 1-butyl-2,3-dimethyl-imidazolium.

30. The method of claim 27 wherein the anionic species of the ionic liquid precursor compound comprises a chloride.

31. The method of claim 30 wherein the alkali metal species is selected from the group consisting of lithium, sodium and potassium.

32. The method of claim 30 wherein the alkaline-earth metal species is selected from the group consisting of magnesium and calcium.

33. A method for purifying a contaminated ionic liquid to form a high-purity ionic liquid having a pH value of 7 and an elemental analysis deviation of less than 0.5 wt % between a calculated elemental analysis and a found elemental analysis for each of carbon, hydrogen and nitrogen, wherein the ionic liquid comprises a cationic species and an anionic species wherein the anionic species is selected from the group consisting of tetrafluoroborate, hexafluorophosphate, bis-trifluoromethanesulfonimide and derivatives thereof, the method comprising the steps of:
(a) extracting the contaminated ionic liquid into a polar extractant to form an extract containing the ionic liquid;
(b) removing any water traces from the extract;
(c) filtering the extract; and
(d) recovering the high-purity ionic liquid from the extract.

34. The method of claim 33 wherein the polar extractant is selected from the group consisting of dichloromethane, 1,2-dichloroethane, tetrachloromethane, chloroform, acetonitrile and mixtures thereof.

35. The method of claim 33 wherein removing step comprises drying the extract over a drying agent.

36. The method of claim 35 wherein the drying agent comprises magnesium sulfate.

37. The method of claim 33 wherein the filtering step comprises filtering the extract through a filter aid comprising at least one of aluminum oxide, Celite, activated carbon and silica gel.

38. The method of claim 33 wherein the filtering step comprises filtering the extract through a filter aid comprising activated carbon.

39. The method of claim 33 wherein the filtering step comprises filtering the extract through a filter aid comprising aluminum oxide.

40. The method of claim 33 wherein the filtering step comprises filtering the extract through a combination of filter aids comprising activated carbon and aluminum oxide.

41. The method of claim 33 wherein the recovering step comprises evaporating off volatile components from the extract to recover the ionic liquid.

42. The method of claim 41 wherein the evaporating step comprises evaporating off the volatile components from the extract at a reduced pressure to recover the ionic liquid.

* * * * *